United States Patent
Blauw et al.

(10) Patent No.: US 8,535,499 B2
(45) Date of Patent: Sep. 17, 2013

(54) MICROFABRICATED LIQUID-JUNCTION REFERENCE ELECTRODE

(75) Inventors: Michiel Blauw, Breda (NL); Javier Gonzalo Ruiz, Sabadell (ES); Mercedes Crego Calama, Geldrop-Mierlo (NL); Sywert H. Brongersma, Eindhoven (DE)

(73) Assignee: Stichting IMEC Nederland, Eindhoven (NL)

( * ) Notice: Subject to any disclaimer, the term of this patent is extended or adjusted under 35 U.S.C. 154(b) by 76 days.

(21) Appl. No.: 13/024,177

(22) Filed: Feb. 9, 2011

(65) Prior Publication Data

US 2011/0192720 A1   Aug. 11, 2011

Related U.S. Application Data (60) Provisional application No. 61/302,670, filed on Feb. 9, 2010.

(51) Int. Cl.
   *G01N 27/26* (2006.01)

(52) U.S. Cl.
   USPC ........... 204/435; 204/414; 204/415; 204/416; 205/775; 977/750; 977/752; 427/122

(58) Field of Classification Search
   USPC ......... 204/414–416, 435; 205/775; 977/750; 977/752; 427/122
   See application file for complete search history.

(56) References Cited

U.S. PATENT DOCUMENTS

| | | | |
|---|---|---|---|
| 4,360,415 A | * | 11/1982 | Brezinski ................... 204/435 |
| 4,980,043 A | | 12/1990 | Tomita et al. |
| 6,419,809 B1 | | 7/2002 | Suzuki et al. |
| 2002/0049389 A1 | * | 4/2002 | Abreu ........................ 600/558 |
| 2003/0168354 A1 | * | 9/2003 | Broadley et al. ............ 205/775 |

FOREIGN PATENT DOCUMENTS

| | | |
|---|---|---|
| EP | 0597203 A2 | 5/1994 |
| JP | 60-171445 A | 9/1985 |
| WO | WO 01/01122 | 1/2001 |
| WO | WO 0101122 * | 1/2001 |

OTHER PUBLICATIONS

Suzuki et al., Sensors and Actuators B, 46, 1998, 146-154.*
Kim, et al. A Miniaturized Electrochemical System with a Novel Polyelectrolyte Reference Electrode and its Application to Thin Layer Electroanalysis, Sensors and Actuators, B 115 (2006), pp. 212-219, Elsevier B.V.
Smith, et al., An Integrated Sensor for Electrochemical Measurements, IEEE Transactions on Biomedical Engineering, Feb. 1986, pp. 83-90, vol. BME-33, No. 2.

(Continued)

*Primary Examiner* — Luan Van
*Assistant Examiner* — Steven Rosenwald
(74) *Attorney, Agent, or Firm* — Knobbe Martens Olson & Bear LLP (57) ABSTRACT

Micromachined reference electrodes for use in miniaturized electrochemical sensors, and methods for fabricating such reference electrodes and electrochemical sensors, for example, as a part of a microfluidic system, are disclosed. Electrochemical measurements allow for inexpensive detection of a wide variety of (bio-)chemical compounds in solution. The reference electrode is one of the main parts of an electrochemical cell. The reference electrode, from which no current is drawn, has a stable, constant potential.

20 Claims, 5 Drawing Sheets

(56) References Cited

OTHER PUBLICATIONS

Suzuki, et al., Micromachined Liquid-Junction Ag/AgCl Reference Electrode, Sensors and Actuators B 46 (1998), pp. 146-154, Elsevier Science S.A.

Van Den Berg, et al., A Micro-volume Open Liquid-junction Reference Electrode for pH-ISFETs, Sensors and Actuators, B1 (1990), pp. 425-432, Elsevier Sequoia, The Netherlands.

Yee, et al., Miniature Liquid Junction Reference Electrode with Micromachined Silicon Cavity, Sensors and Actuators, 15 (1988), pp. 337-345, Elsevier Sequoia, The Netherlands.

European Search Report for European Patent Application No. 11153838.5-2204 dated May 9, 2011 by European Patent Office.

Polk et al., "Ag/AgCl microelectrodes with improved stability for microfluidics", Sensors and Actuators B, Elsevier Sequoia S.A., Lausanne, CH, vol. 14, No. 1, Mar. 30, 2006, pp. 239-247.

* cited by examiner

MICROFABRICATED LIQUID-JUNCTION REFERENCE ELECTRODE

CROSS REFERENCE TO RELATED APPLICATIONS

This application claims priority under 35 U.S.C. §119(e) to U.S. provisional patent application 61/302,670 filed on Feb. 9, 2010, which application is hereby incorporated by reference in its entirety.

BACKGROUND OF THE INVENTION

1. Field of the Invention

This invention relates to micromachined reference electrodes, for example, for use in miniaturized electrochemical sensors, and to methods for fabricating such reference electrodes and electrochemical sensors, for example, as a part of a microfluidic system.

2. Description of the Related Technology

Electrochemical measurements allow for inexpensive detection of a wide variety of (bio-)chemical compounds in solution. The reference electrode is one of the main parts of an electrochemical cell. The reference electrode, from which no current is drawn, has a stable, constant potential. There are two kinds of electrochemical sensors that need a reference electrode: amperometric sensors and potentiometric sensors. Amperometric sensors comprise a sensing electrode or working electrode, a counter electrode and a reference electrode. Potentiometric sensors comprise an ion-selective electrode (ISE) as a working electrode and a reference electrode.

In the case of amperometric sensors, a current is generated between the sensing electrode and the counter electrode when a compound that needs to be detected is oxidized or reduced on the sensing electrode. The current depends on the concentration of the compound. The current also depends on the sensing electrode potential, which is generated by an external power source. The sensing electrode is defined relative to the reference electrode potential. Therefore, accurate and reproducible current measurements can only be obtained if a stable reference electrode potential is available.

In the case of potentiometric sensors, the measured parameter is the open circuit voltage (OCV) between the ISE and the reference electrode. The ISE shows a high selectivity towards certain compounds, where the OCV changes as a function of the concentration of these compounds.

As can be deduced from the previous two paragraphs, the reference electrode is a crucial part of an electrochemical sensor. An unstable reference electrode in an amperometric sensor results in a shift of the sensing electrode potential, which affects the output current. The situation is even more detrimental in potentiometric sensors, where any fluctuation of the reference electrode potential is fully reflected in the output signal. An instable reference electrode inevitably results in malfunctioning of the electrochemical sensor.

Existing systems often use an external, macroscopic reference electrode or a quasi-reference electrode, which is directly exposed to the sample solution. External, macroscopic reference electrodes typically have a size of approximately 10 cm. An Ag/AgCl electrode, among other materials, is often used in an external, macroscopic reference electrode, where the Ag/AgCl electrode is often immersed in a solution that contains 3 molar KCl and saturated AgCl. The voltage of an Ag/AgCl electrode depends on the chloride concentration of the solution in contact with the electrode. Therefore, if a constant voltage is needed, the chloride concentration needs to be kept constant. In order to do that, the KCl solution in the reference electrode is physically separated from the sample solution by means of an electrolyte bridge or a porous, ceramic plug. As a result, the chloride concentration does not change significantly. At the same time, there is contact with the external solution that contains the other electrodes trough the electrolyte bridge or the porous, ceramic plug. However, such a macroscopic reference electrode configuration that is based on glass tubes is difficult to miniaturize. Moreover, a liquid-junction potential is established across a porous, ceramic plug, which adds up to the reference potential leading to a misestimating of the sensing electrode potential.

Various miniature electrochemical sensors have been developed. The fabrication technologies for these devices and their performance have advanced sufficiently to realize their commercialization. However, one of the main problems that have restricted their application is the unavailability of a reliable and durable miniature reference electrode. Miniaturized electrochemical sensors often contain a quasi-reference electrode. In this case, the electrode, e.g. Ag/AgCl electrode, is not submerged in a separate KCl solution but in the sample solution together with the other electrodes. Two stability problems are inherent to this approach. First, the KCl concentration, which is related to the reference electrode voltage, is not constant. Second, interfering redox reactions with the analyte and other substances may take place at the reference electrode.

Microfabrication of reference electrodes can be done by micromachining of KCl solution reservoirs in silicon, for example, by means of KOH etching. In some cases, a plug may be needed to increase the lifetime, although this may lead to an increase of the junction potential. For example, pyramidal reservoirs can be created by KOH etching leading to a pinhole at one side, where the pinhole is in contact with the sample solution during operation. In general, it is difficult to use this approach for the integration of a larger microfluidic system due to constraints of the KOH etching process. For example, there are constraints to the shapes of reservoirs and channels that can be fabricated by means of KOH etching. Moreover, it is only possible to etch silicon in a KOH solution. Silicon is a relatively expensive material and it is preferably replaced by other materials such as glass and polymers.

The lifetime of a liquid-junction reference electrode is related to the decrease of the electrolyte concentration in the reference electrode reservoir, for example, as a result of effusion and outflow from the reference electrode reservoir, leading to a change of the reference potential. In order to slow down the effusion of KCl from the reference electrode, the pinhole can be closed by a porous silicon membrane acting as a diffusion barrier, for example, as reported by R. L. Smith and D. C. Scott in "An integrated sensor for electrochemical measurements", IEEE Trans. Biomed. Eng. 33, 83 (1986). However, process integration of porous silicon can be difficult and thus the reproducibility of this approach is lacking. Diffusion barriers other than porous silicon can be used such as porous silica glass and polymers. The fabrication and integration of porous materials is quite complex because it requires wet chemical processes that are not easily scaled up. Alternatively, instead of using a diffusion barrier, the pyramidal reservoir can be filled with a hydrogel solution to avoid leaching out of the KCl solution, for example, as reported by A. van den Berg et al. in "A micro-volume open liquid-junction reference electrode for pH-ISFETs", Sensors and Actuators B 1, 425 (1990). However, using this approach the reference electrode potential drift could not be reduced below 0.1 mV·h$^{-1}$. In general, the use of a porous plug or a hydrogel to reduce the diffusion of ions may increase the liquid-junction potential in an unpredictable manner. Moreover, the response time to a change in the sample solution can increase as a result of the slower ion diffusion in the porous plug or the hydrogel.

More advanced techniques for the microfabrication of liquid-junction reference electrodes, leading to the creation of larger microfluidic systems, have been reported. For example, a method is described in U.S. Pat. No. 6,419,809 for fabricating a complete reference electrode in silicon using microfabrication techniques. The microfluidic part comprises a reservoir, a channel and a pinhole. However, a reliable diffusion barrier was only obtained by closing the pinhole with a polymer plug. Typical lifetime values for the systems described in U.S. Pat. No. 6,419,809 are in the order of one day. Moreover, a polymer plug may influence the junction potential in an unpredictable manner and complicates the fabrication process. The lifetime of the reference electrode is also dependent on the durability of the internal electrode, usually an Ag/AgCl electrode, and not only on the stability of the KCl concentration. Other internal electrode materials and electrolytes can also be used if this improves the reference electrode lifetime.

SUMMARY OF CERTAIN INVENTIVE ASPECTS

One inventive aspect relates to a miniaturized free-diffusion liquid-junction reference electrode with a good lifetime and a good response time, and to an integrated microfluidic system comprising such a miniaturized free-diffusion liquid junction reference electrode.

In one aspect, a liquid-junction reference electrode comprises: a reservoir for containing an electrolyte; an internal electrode in the reservoir that is to be in contact with the electrolyte; a pinhole for providing a fluidic contact to a sample solution; and a high-aspect-ratio channel connecting the reservoir and the pinhole, where the electrolyte can freely diffuse from the reservoir to the pinhole through the high-aspect-ratio channel. It is an advantage of providing a high-aspect-ratio channel connecting the reservoir and the pinhole that the electrolyte concentration in the reservoir decays very slowly. For example, the channel can have an aspect ratio in the order of about 100 up to 10000:1. The channel can have an inlet part connected to the reservoir, an outlet part connected to the pinhole, and a meandering part in between the inlet part and the outlet part. As a result, the liquid-junction reference electrode has a good lifetime, for example, in the order of one month up to one year, if the stability of the internal electrode is not considered. Another advantage is that the need for providing a porous plug or a hydrogel in the channel is avoided, so that a low junction potential and a fast response to a change of the sample solution can be obtained. Hence the high-aspect-ratio channel preferably does not contain an ion-conduction plug but it may do so optionally.

In certain embodiments the internal electrode can for example be an Ag/AgCl electrode. In this case, the electrolyte can consist of a high-concentration KCl solution. However, other materials can be used for forming the internal electrode, such as for example iridium oxide (IrOx).

The reference electrode can further comprise at least one additional electrolyte reservoir connected to at least one additional high-aspect-ratio channel, where the at least one additional electrolyte reservoir and the at least one additional high-aspect-ratio channel are connected to and provided in between the internal electrode reservoir and the pinhole. It is an advantage of such a higher order system that the reference electrode lifetime can be improved further.

The liquid-junction reference electrode can further comprise additional elements such as an external electrical contact to the internal electrode, means for filling the electrolyte reservoir comprising the internal electrode, means for filling the at least one additional electrolyte reservoir, and additional electrodes forming an ion conductivity sensor. The means for filling a reservoir can for example comprise an opening and a relatively wide channel between the opening and the reservoir.

The reference electrode may further comprise an electrically conductive strip, e.g. a metal strip, forming a low impedance bypass for the high-aspect-ratio channel. The electrically conductive strip is preferably provided for connecting the inlet part of the high-aspect-ratio channel closest to the electrolyte reservoir comprising the internal electrode and the outlet part of a high-aspect ratio channel, preferably the outlet part of the high-aspect ratio channel closest to the pinhole. It is an advantage of providing such a metal strip that it forms a low impedance bypass around the high-aspect-ratio channels. This reduces the AC impedance of the reference electrode and can thus improve the electronic stability of an external potentiostat controlling the voltages on the electrodes.

The liquid-junction reference electrode can be fabricated using standard micromachining techniques, and using cheap materials, for example, glass and photo-patternable polymers.

One inventive aspect relates to a microelectrochemical cell comprising a liquid-junction reference electrode as described above and a method for fabricating such a microelectrochemical cell.

Some objects and advantages for certain inventive aspects have been described herein above. Of course, it is to be understood that not necessarily all such objects or advantages may be achieved in accordance with any particular embodiment. For example, those skilled in the art will recognize that the invention may be embodied or carried out in a manner that achieves or optimizes one advantage or group of advantages as taught herein without necessarily achieving other objects or advantages as may be taught or suggested herein. Further, it is understood that this summary is merely an example and is not intended to limit the scope of the invention. The invention, both as to organization and method of operation, together with features and advantages thereof, may best be understood by reference to the following detailed description when read in conjunction with the accompanying drawings, which exemplary in nature. The scope of the invention is determined by the claims.

DETAILED DESCRIPTION OF CERTAIN ILLUSTRATIVE EMBODIMENTS

In the following detailed description, numerous specific details are set forth in order to provide a thorough understanding of the invention and how it may be practiced in particular embodiments. However, it will be understood that the present invention may be practiced without these specific details. In other instances, well-known methods, procedures and techniques have not been described in detail, so as not to obscure the present invention. While the present invention will be described with respect to particular embodiments and with reference to certain drawings, the invention is not limited hereto. The drawings included and described herein are schematic and are not limiting the scope of the invention. It is also noted that in the drawings, the size of some elements may be exaggerated and, therefore, not drawn to scale for illustrative purposes.

Furthermore, the terms first, second, third and the like in the description, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, bottom, over, under and the like in the description are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising" should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B.

Certain embodiments relate to micromachined free-diffusion liquid-junction reference electrodes with better performance than prior art solutions, that is, having a longer lifetime and a shorter response time. Certain embodiments relate to methods for fabricating such micromachined liquid junction reference electrodes that are less complex and have lower cost than prior art methods. The size scaling of the microfluidic reference electrodes, which is made possible by the use of micromachining techniques, results in a higher yield of devices per process run. Moreover, as micromachining techniques can largely be automated, an increase of the production volume and a decrease of the device cost can be obtained.

A liquid-junction reference electrode according to one embodiment comprises: a reservoir for containing an electrolyte; an internal electrode in the reservoir that is to be in contact with the electrolyte; a pinhole for providing a fluidic contact to a sample solution; and a high-aspect-ratio channel connecting the reservoir and the pinhole, wherein the electrolyte can freely diffuse from the reservoir to the pinhole through the high-aspect-ratio channel. It is an advantage of providing a high-aspect-ratio channel connecting the reservoir and the pinhole that the electrolyte concentration in the reservoir decays very slowly. For example, the channel can have an aspect ratio in the order of about 100 up to 10000:1. The channel can have an inlet part connected to the reservoir, an outlet part connected to the pinhole, and a meandering part in between the inlet part and the outlet part.

Certain illustrative embodiments are described wherein the internal electrode is an Ag/AgCl electrode and wherein the electrolyte is a KCl solution. However, the invention is not limited thereto. Other suitable materials known to a person skilled in the art may be used, such as for example an IrOx internal electrode and a fixed pH solution such as phosphate buffered saline. For IrOx electrodes the pH dependence of the electrode potential is well-established. Moreover, IrOx electrodes exhibit a minimal long-term drift of their potential over a wide pH range. It also implies that the electrode potential is very stable in a fixed pH solution. An example of a fixed pH solution is phosphate buffered saline (PBS). A surplus of KCl is added to PBS to minimize the liquid-junction potential. These characteristics make IrOx an interesting material for use in a reference electrode. Using IrOx as the internal electrode material and filling the reservoir with PBS, a reference electrode with a good stability can be obtained.

It is an advantage of a micromachined liquid-junction reference electrode according to one embodiment that the electrolyte concentration in the internal electrode reservoir decays very slowly, and thus it has a long lifetime, for example, in the order of one month up to one year. This is accomplished by connecting the electrolyte reservoir comprising the internal electrode by means of a high-aspect-ratio channel, which has, for example, an aspect ratio in the order of about 100 up to 10000:1, to a pinhole that is in contact with the sample solution. Free ion diffusion is allowed in the high-aspect-ratio channel, that is, no hydrogel, polyelectrolyte, or porous ceramic is provided in the channel, thereby avoiding liquid-junction potential drifts and shifts. As a result, the good properties of a free-diffusion liquid-junction reference electrode, that is, a low junction potential and an instant response to a change of the sample solution, are maintained while the diffusion of KCl ions is strongly reduced as compared to prior art miniaturized reference electrodes.

Furthermore, the use of higher order systems wherein several electrolyte reservoirs are connected by high-aspect-ratio channels, can further improve the lifetime of the reference electrode.

Although a hydrogel, a polyelectrolyte or a porous ceramic plug is not provided in the channel of preferred embodiments, such an ion-conducting plug can be added optionally in some embodiments, for example, to prevent leaking of the electrolyte or evaporating of the solvent from the reservoir. Alternatively, the reservoir and the channel can be filled with an ionic liquid, which does not evaporate, as a solvent for KCl.

Standard microfabrication techniques can be used to make liquid-junction reference electrodes according to one embodiment. In preferred embodiments the high-aspect-ratio channel has a folded geometry to obtain a large channel length on a small chip area. By making the compact channel geometry with microfabrication technologies, the whole system can be integrated on a relatively small area of a microfluidic chip. Several materials can be used as the substrate material such as silicon, glass, and polymers such as SU8, BCB, PDMS, PMMA and polycarbonate. It is an advantage of using polymers that they can be formed by photo-patterning and molding.

Figure 5:
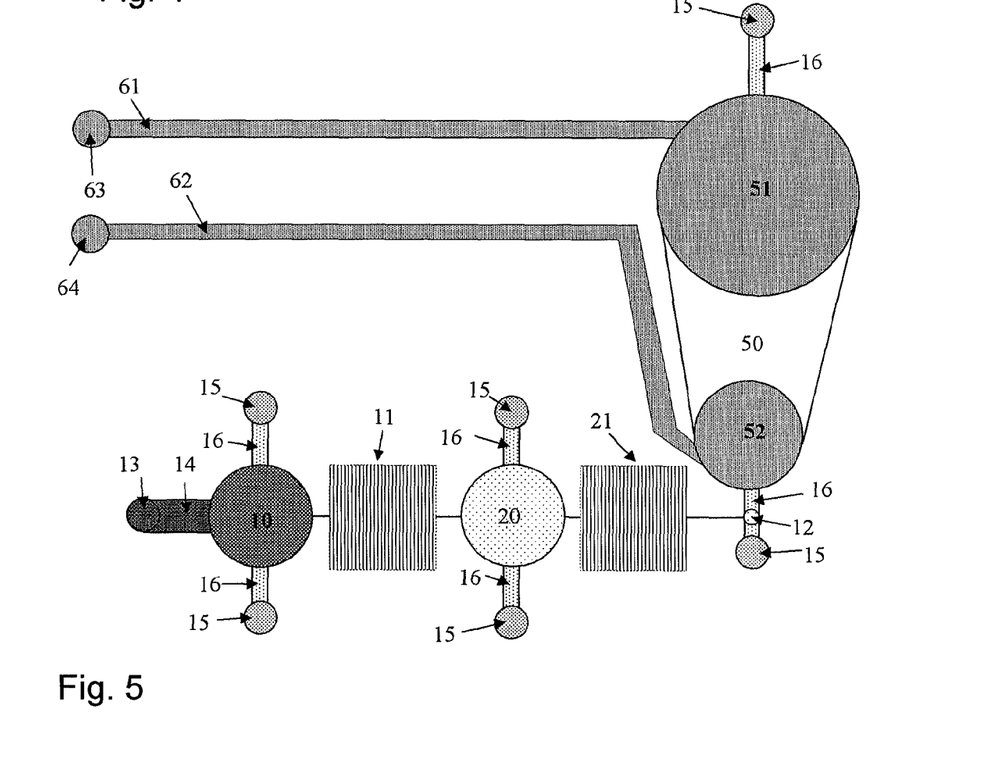
FIG. 5 schematically shows the geometry of a microelectrochemical cell with a 2nd order reference electrode system according to one embodiment.

A miniaturized reference electrode according to one embodiment can be integrated on a chip, for example, together with a reactor chamber, a liquid inlet, a liquid outlet, electrical connections and other components such as pumps and valves, thereby creating a lab-on-a-chip. The external power supply can be an integrated circuit that can be bonded to the microfluidic system, thereby creating a system-in-package (SiP). Such a miniaturized system is further referred to as a microelectrochemical cell (MECC) and an exemplary embodiment is schematically illustrated in FIG. 5. Applications wherein such a miniaturized system can be used are, for example, point-of-care medical applications such as a continuous glucose monitoring system, kidney damage prevention, and pregnancy test, medical diagnostics equipment, environmental pollution monitoring, control of agricultural conditions (agricultural growth control), food processing analysis, monitoring of conditions during transport of fresh products, biochemical analysis, determination of electrochemical salt concentration, micro total analysis systems (µTAS), and lab-on-a-chip applications.

Figure 1A:
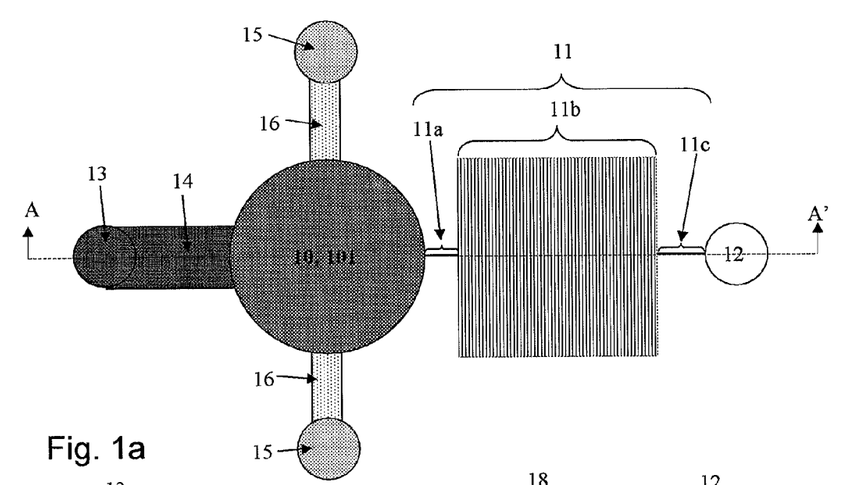
FIG. 1(a) shows a schematic layout of a 1st order system according to one embodiment.
Figure 1B:
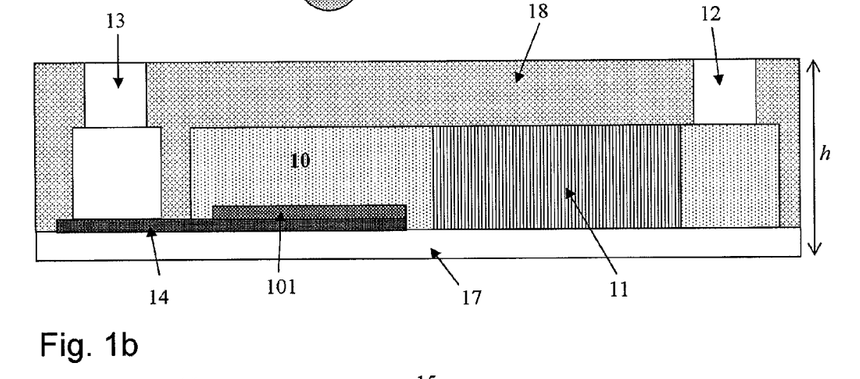
FIG. 1(b) shows a cross-section along line A-A'.

FIG. 1 shows a schematic layout of a $1^{st}$ order system or reference electrode according to one embodiment. FIG. 1(a) shows a schematic top view of the system, and FIG. 1(b) shows a cross-section along line A-A'. The system comprises a reservoir 10 which contains an electrolyte solution (such as a KCl solution) for creating a reliable reference potential. An internal electrode 101 (such as an Ag/AgCl electrode) is present at a bottom of the electrolyte reservoir 10, wherein the internal electrode 101 may cover the whole bottom of the electrolyte reservoir 10 to exclude edge effects. In the example shown in FIG. 1, the internal electrode reservoir 10 has a circular shape but any other suitable shape can be used. The internal electrode reservoir 10 is connected to one end of a high aspect ratio channel 11, an opposite end of the channel 11 being connected to a pinhole 12. The high aspect ratio channel comprises an inlet part 11a connected to the internal electrode reservoir 10, an outlet part 11c connected to the pinhole 12 and a meandering part 11b in between the inlet part 11a and the outlet part 11c. The electrolyte can freely diffuse from the internal electrode reservoir 10 to the pinhole 12 through the high-aspect-ratio channel 11. The pinhole 12 provides a fluidic contact and may be further connected to an external liquid reservoir, for example, to an electrochemical cell containing a sample solution to be analyzed. An electrical contact 13 is provided to the internal electrode 101 via an electric contact line 14. Filling means (openings 15 and wide channels 16) are provided for filling the internal electrode reservoir 10 with an electrolyte solution, for example, a KCl solution for Ag/AgCl electrodes, with a known concentration after fabrication. These filling means 15, 16 are preferably provided as it may not be possible to fill the internal electrode reservoir 10 through the long and meandering high-aspect-ratio channel 11, and to enable escape of air bubbles from the system. The system can be provided on a substrate 17, for example, a glass substrate, and the micromachined structure 18 can be formed in a polymer material, for example SU8.

In certain embodiments, the channel 11 preferably has an aspect ratio in the range of about 100 up to 10000:1, such as 1000:1. The aspect ratio is defined by the ratio of the length and the width of the channel. The cross-section of the channel 11 can have an arbitrary shape but using micromachining techniques a nearly square cross-section can be obtained. The high aspect ratio can be realised on a relatively small chip area by folding the long and narrow channel into a meandering structure.

In a reference electrode according to one embodiment, the channel 11 has typically a width in the order of about 10 µm to 100 µm, such as 20 µm. The internal electrode reservoir 10 has typically a size in the range from about 1 mm to 10 mm in diameter, such as 3 mm. The filling openings 15, channels 16, pinhole 12, electrical contact 13 and electrical contact line 14 have typically a width in the order of 1 mm, depending on the requirements of the external connections. The total height h of the microfluidic system is typically in the order of about 10 µm up to 100 µm, such as 20 µm, depending on the materials and processes used.

Using microfabrication technologies, a high-aspect-ratio channel 11 comprising a meandering part 11b can be formed, in which free-diffusion leads to a well-defined liquid-junction potential. The liquid junction potential is relatively low in case of a KCl solution. No hydrogel, polyelectrolyte, or porous ceramic plugs, which influence the liquid-junction potential, are needed. However, an ion-conducting plug can be placed in the channel optionally, for example, to prevent evaporation of the liquid from the reservoir.

Figure 2:
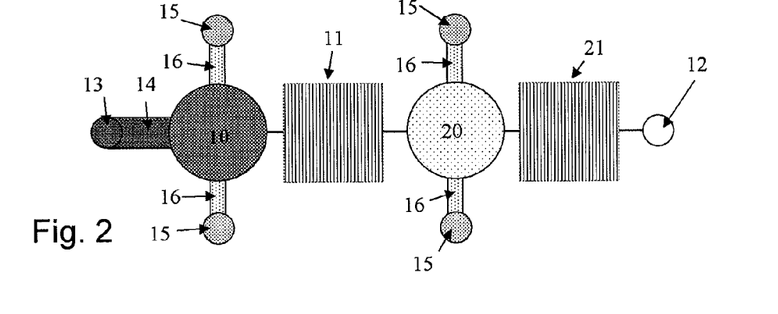
FIG. 2 shows a schematic layout of a 2nd order system according to one embodiment.
Figure 3:
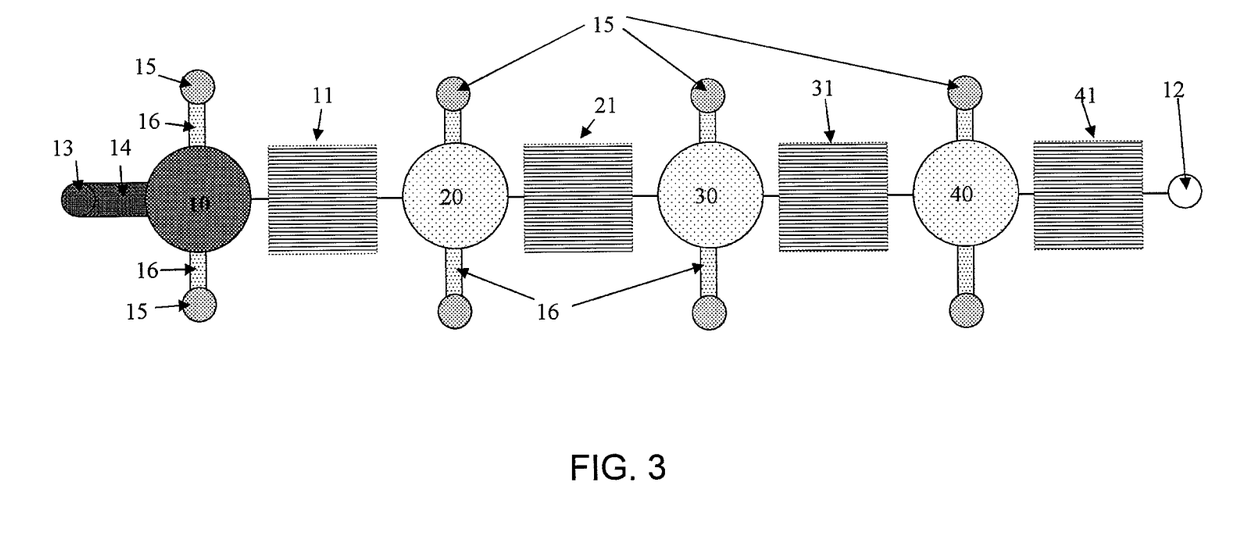
FIG. 3 shows a schematic layout of a 4th order system according to one embodiment.

In certain embodiments, the system can comprise a chain of reservoirs coupled by means of high-aspect-ratio channels. In such higher order embodiments the stability of the electrolyte concentration in the internal electrode reservoir 10 at an end of the chain of reservoirs is further improved. For example, the layout of a $2^{nd}$ order system (comprising two coupled reservoirs 10, 20) is shown in FIG. 2 and the layout of a $4^{th}$ order system (comprising four coupled reservoirs 10, 20, 30, and 40) is schematically shown in FIG. 3. Coupling between subsequent reservoirs and coupling between the last reservoir (20 in FIG. 2, 40 in FIG. 3) in the chain and the pinhole 12 is obtained by providing high-aspect-ratio channels (11, 21, 31, and 41) preferably comprising a meandering part. In the context of one embodiment, the term 'internal electrode reservoir' or 'internal electrode electrolyte reservoir' is used for indicating an electrolyte reservoir 10 wherein an internal electrode 101 is provided.

The lifetime of exemplary $1^{st}$ order systems was calculated, for a system based on an Ag/AgCl internal electrode and KCl as an electrolyte, without considering the influence of the internal electrode on the lifetime. A $1^{st}$ order system shows an exponential decay of the KCl concentration in the internal electrode reservoir 10 as a function of time. For such a system, the lifetime is given by the characteristic time of the exponential decay. The end-of-life of a system depends on the application and the specifications related to the maximum allowed reference potential change. Based on these specifications, the end-of-life of a device can be traced back from the corresponding change of the KCl concentration. For a first order system comprising an Ag/AgCl internal electrode with an electrolyte reservoir diameter of about 4 mm, a channel width of about 10 micrometer, a channel length of about 80 mm and a pinhole diameter of about 1 mm, the calculated lifetime (the characteristic time of the exponential decay of the KCl concentration in the internal electrode reservoir 10) is in the order of one year. For a first order system comprising an Ag/AgCl electrode with an electrolyte reservoir diameter of about 4 mm, a channel width of about 100 micrometer, a channel length of about 40 mm and a pinhole diameter of about 1 mm, the projected lifetime is in the order of one month.

Figure 4:
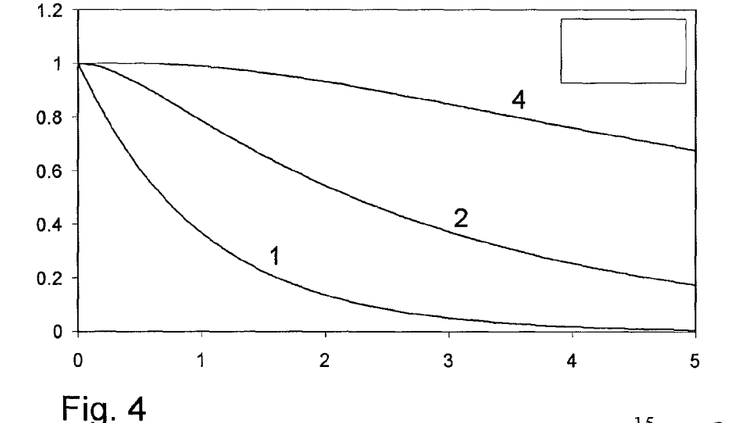
FIG. 4 shows numerical simulation results of the temporal behavior of the ion concentration in an internal electrode electrolyte reservoir for a 1st order, a 2nd order and a 4th order system according to certain embodiments. The Y-axis has as unit dimensionless concentration, the X-axis has as unit dimensionless time, the lower curve (1) relates to first order, the middle curve (2) relates to second order, and the upper curve (4) relates to fourth order.

Lifetimes of higher order systems were calculated numerically. The temporal behavior of the electrolyte concentration in the internal electrode reservoir 10 containing the Ag/AgCl electrode 101 has principally a zero derivative for higher order systems at the begin of the measurement, that is, after inserting the pinhole 12 in a sample solution, where free-diffusion starts throughout the microfluidic system. On the contrary, a $1^{st}$ order system having a single reservoir 10 always shows exponential decay of the electrolyte concentration in the internal electrode reservoir 10, having a finite derivative different from zero at the begin of the measurement. A numerical simulation comparing the temporal behavior of the ion concentration in an internal electrode reservoir 10 of a $4^{th}$ order system, a $2^{nd}$ order system, and a $1^{st}$ order system is given in FIG. 4. In FIG. 4, the Y-axis has as unit dimensionless concentration and the X-axis has as unit dimensionless time. The lower curve (a) relates to a $1^{st}$ order system, the middle curve (2) relates to a $2^{nd}$ order system and the upper curve (4) relates to a $4^{th}$ order system. The $1^{St}$ order system shows an exponential decay as expected. The characteristic time of the exponential decay, which is the lifetime of the system, is used to make the time scale dimensionless. Connecting several reservoirs with identical dimensions strongly improves (reduces) the decay of the electrolyte concentration in the internal electrode reservoir 10 as a function of time, and thus improves the lifetime of the system. The electrolyte concentration of the $4^{th}$ order system is nearly constant within the characteristic time of the $1^{st}$ order system, leading to a nearly constant internal electrode potential. In an actual application the reservoir diameter and the channel length and width can be selected such that the absolute lifetime matches the specifications.

FIG. 5 shows an example of a microfluidic system, in particular, an integrated microelectrochemical cell (MECC) with a reference electrode according to one embodiment. Such a complete, integrated MECC can be made using microfabrication techniques. In the example shown in FIG. 5, the reference electrode is a $2^{nd}$ order system as in FIG. 2. The $2^{nd}$ order reference electrode system is connected to a reactor chamber 50 in which a sensing/working electrode 51 and a counter electrode 52 are located. The sensing electrode 51 is electrically connected to a first electrical contact line 61 and the counter electrode 52 is electrically connected to a second electrical contact line 62.

The working electrode or sensing electrode 51 and the counter electrode 52 can have an arbitrary shape. For example, they can have a disc shape as shown in FIG. 5. Other shapes, such as for example rectangular or interdigitated shapes are also possible. Alternatively, the counter electrode can be located tangentially around a disc shaped working electrode. The working electrode and the counter electrode can also be placed in two reservoirs separated by a short channel to improve the detection performance.

In these configurations, the liquid contact (pinhole 12) of the reference electrode is preferably placed as close as possible to the counter electrode and at a side opposite to the side of the working electrode (i.e. at a location that is not in between the working electrode and the counter electrode) in order to minimize the influence of the Ohmic drop between the working electrode and the counter electrode in the electrochemical cell. A large Ohmic drop would lead to a discrepancy between the potential that is applied by the external source and the working electrode potential. The Ohmic drop can also be reduced by using currents that are in the order of one µA and less.

Figure 6:
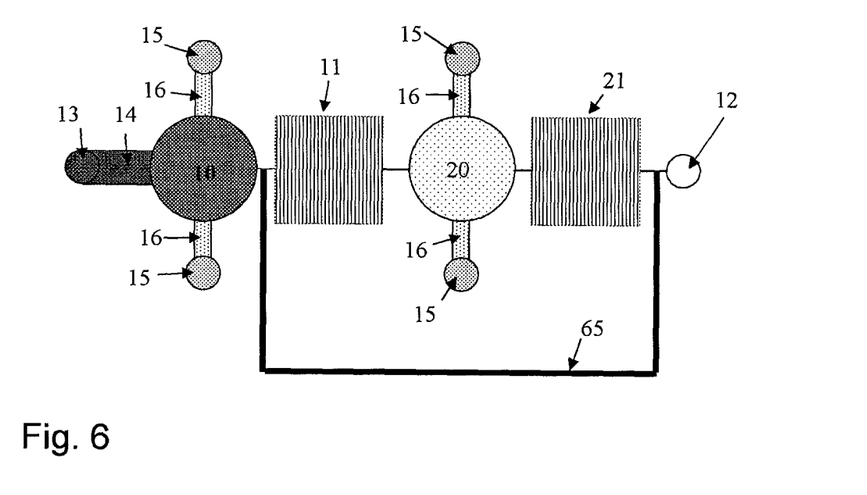
FIG. 6 schematically shows a 2nd order system comprising a low impedance bypass according to certain embodiments.

An external potentiostat (not illustrated) can be used to control the voltages on the working electrode and the counter electrode relative to the reference potential. For high AC impedances, the external potentiostat can start to oscillate. Therefore, in order to reduce the AC impedance of the reference electrode, a low impedance bypass such as for example a metal strip 65 can be provided, as illustrated in FIG. 6 for a $2^{nd}$ order system. The metal strip 65 is provided between the inlet part of the high-aspect-ratio channel 11 closest to the internal electrode electrolyte reservoir 10 and the outlet part of the high-aspect-ratio channel 21 closest to the pinhole 12. The other end of the metal strip 65 is provided near the pinhole 12. One end of the metal strip 65 is provided near the internal electrode electrolyte reservoir 10. It is not connected to the internal electrode 101. The metal strip 65 is located in the channel, on the insulating substrate 17, and immersed in the electrolyte. By immersing the metal strip 65 in the electrolyte it is capacitively coupled to the channel. The surface area in contact with the liquid (electrolyte) is preferably sufficiently large. Calculations show that the surface contact area needed is in the order of about 1 mm$^2$. This means that a metal strip of 1 mm wide in a channel of 1 mm wide would be suitable. If the channel is not sufficiently wide to yield sufficient surface contact area, the part of the channel 11 between the metal strip 65 and the internal electrode reservoir 10 and/or the part of the channel 21 between the metal strip 65 and the pinhole 12 is preferably wider than the meandering part of the high-aspect-ratio channels.

The low impedance bypass provided by the metal strip 65 can improve the electronic stability of the external potentiostat. High DC impedances may be less of a problem because the DC current to the Ag/AgCl electrode is mostly less than about 50 pA for commercial potentiostats. For most applications, the DC impedance can be as high as about 20 MΩ because the potential drop along the channel remains less than about 1 mV in that case. For example, a 150 nm thick and 1 mm wide Pt strip of 18 cm length has an impedance of about 12Ω and can act as a low-resistance bypass.

In a microelectrochemical cell as illustrated in FIG. 5, the electrical contacts of contact lines 14, 61, and 62 are accessible for external read-out electronics through pinholes 13, 63 and 64, respectively. The reactor chamber 50 is accessible for external liquid reservoirs containing the sample solution through pinholes 15 and channels 16. The sensing/working electrode 51 can be modified, for example, with enzymes, in order to enhance the sensitivity to biochemical compounds.

Electronic circuits are needed to control the voltages on the electrodes and to measure the generated currents. For example, the microfluidic system that is integrated on a single chip can be plugged into an electronic read-out device (cartridge fabrication) or it can be bonded to an electronics chip (system in a package fabrication). In this way, the microfluidic part can be fabricated separately from the electronics, which may result in lower production costs. In the case that the microfluidic chip can be changed as a cartridge, the electronics can be used for several microfluidic chips over a long period of time largely exceeding the lifetime of the microfluidic chip, thereby further lowering the cost of the total system. Furthermore, additional electronic functions such as digital processing and RF communication of the measurement results from a remote location to a central database can be added to the total system.

Figure 7:
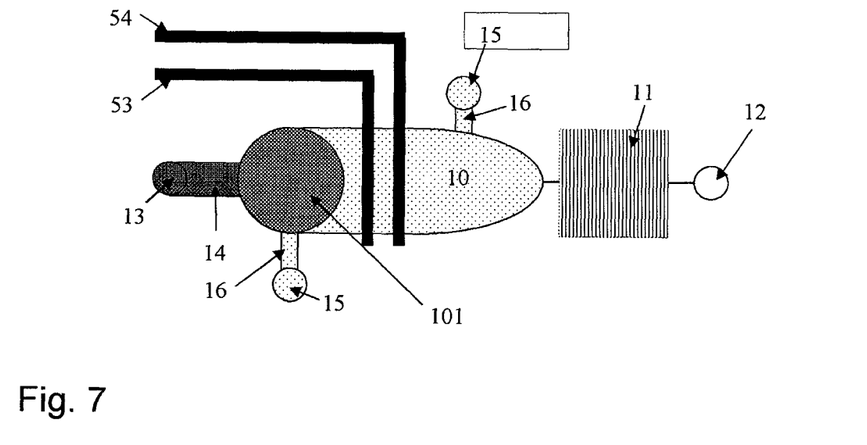
FIG. 7 shows a reference electrode according to one embodiment, with an internal KCl concentration sensor for feedback to an electronic reference potential compensation.

Although changes of the electrolyte concentration are minimized using the above-mentioned techniques, it is possible to further improve the stability of the miniaturized reference electrode by electronic compensation techniques. For example, a micromachined liquid-junction reference electrode according to one embodiment may comprise an ion conductivity sensor in the internal electrode reservoir 10. For example, the chloride concentration is measured in the case that the internal electrode reservoir contains an Ag/AgCl internal electrode 101. As illustrated in FIG. 7, an ion conductivity sensor comprises two electrodes 53 and 54 which are located partially in the reservoir 10 next to the internal electrode 101. The ion conductivity sensor electrodes 53 and 54 are preferably made of a material that does not induce chemical reactions in the reservoir. Preferably the ion conductivity sensor electrodes 53 and 54 are made of platinum because this is the most inert material. An alternating voltage is applied between the two electrodes 53 and 54 of the ion conductivity sensor and an electrical current is measured. The electrical current is a measure of the electrolyte concentration in the reservoir 10.

Changes of the reference electrode potential that are caused by changes of the electrolyte concentration in the reservoir 10 can be compensated electronically by using the output of the ion conductivity sensor. The reference electrode potential depends in a predictable manner on the electrolyte concentration, for example, the KCl concentration. However, all electrochemical reactions are specified relative to a standard reference electrode potential, that is, the reference electrode potential at a certain concentration of the KCl solution. Using analog electronics, it is possible to convert the changes of the measured current of the ion conductivity sensor to a voltage and to add it to the reference electrode potential. As a result, the output of the analog circuit is corrected automatically for ion concentration changes directly without any digital processing. Digital processing would need AD-DA conversion, which consumes relatively much power. The ion conductivity of the KCl concentration in the reservoir 10 can be measured without gas bubble formation for voltages below the electrolysis potential of pure water (−1.23 V).

Figure 9:
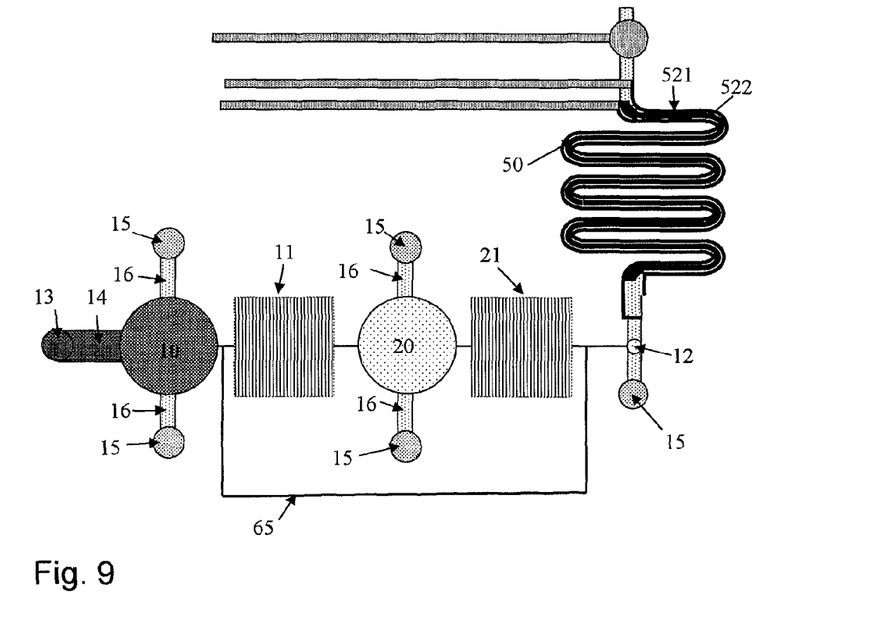
FIG. 9 schematically shows the geometry of a microelectrochemical cell with a 2nd order reference electrode system according to one embodiment, wherein the reactor chamber comprises a high-aspect-ratio channel.

FIG. 9 schematically illustrates an embodiment of a microelectrochemical cell comprising a second order reference electrode according to one embodiment. In this embodiment, the reactor chamber 50 has the form of a long and narrow channel, in the example shown a meandering channel, through which an analyte solution can flow. In this channel two parallel or interdigitated working electrodes 521, 522 are provided with distinct potentials. These potentials are selected such that the molecules are oxidized at one electrode and reduced at the other electrode. If the channel width is sufficiently small, for example in the order of about 1 micrometer or less, redox cycling can increase the sensitivity significantly. Redox cycling can occur with this geometry when the lateral diffusion rate is substantially larger than the longitudinal convection rate. There may be a need to adjust the flow rate of the analyte to achieve this. In this way a compact flow-through detector with high sensitivity can be obtained. The system also comprises an additional counter electrode, such that the potentials on the two parallel electrodes can be set independently to optimize redox cycling.

A process for fabricating a system according to one embodiment may be based on silicon/glass micromachining, polymer molding and photosensitive-polymer patterning. By using lithographic techniques, a strong miniaturization and a good critical dimension control can be obtained.

Figure 8:
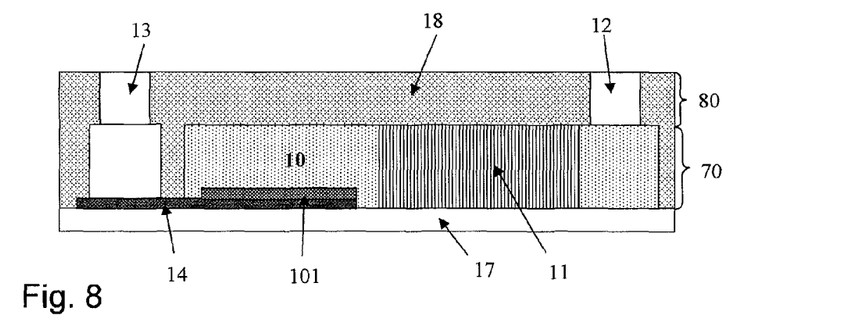
FIG. 8 shows a cross-section of a 1st order system according to one embodiment, indicating the channel layer and the contact layer.

Different approaches can be used for the fabrication. In a first approach, the electrical contact line 14 and the Ag/AgCl electrode 101 are formed on the substrate 17, for example, a glass substrate. The channel layer can be formed on a separate temporary carrier substrate, for example, by photosensitive-polymer patterning. The channel layer, which is indicated with 70 in FIG. 8, is the part of the system where liquids may be present in the final device. The polymer channel layer may be bonded to the temporary carrier wafer by means of a temporary adhesive. After fabricating the channel layer 70, it is removed from the temporary carrier substrate and bonded to the substrate 17 comprising the electrical contact line 14 and the Ag/AgCl electrode 101. The channel layer can also be bonded to the substrate 17 first and be released from the carrier wafer afterwards. The contact layer can then be formed on a separate temporary carrier substrate, for example, by photosensitive polymer patterning. The contact layer, which is indicated with 80 in FIG. 8, is the part of the system where electrical contacts and fluidic contacts are provided. The polymer contact layer 80 may be bonded to the temporary carrier wafer by means of a temporary adhesive. After fabricating the contact layer 80, it is removed from the temporary carrier substrate and bonded to channel layer 70. The contact layer 80 can also be bonded to the channel layer 70 first and be released from the carrier wafer afterwards.

In a second approach, the electrical contact line 14 and the Ag/AgCl electrode 101 are formed on the substrate 17, for example, a glass substrate. In this case, the channel layer 70 and the contact layer 80 are formed as a multilayer stack on a temporary carrier substrate, for example by photosensitive polymer patterning. The polymer multilayer stack may be bonded to the temporary carrier substrate by means of a temporary adhesive. After fabricating the contact layer 80 and the channel layer 70, the polymer structure is removed from the temporary carrier substrate and bonded to the substrate 17 with the electrical contact line 14 and the Ag/AgCl electrode 101. The multilayer stack can also be bonded to the substrate 17 first and be released from the carrier wafer afterwards.

In a third approach, the channel layer 70 can be formed directly on the substrate 17 with the electrical contact line 14 and the Ag/AgCl electrode 101. Subsequently, the contact layer 80 can be fabricated on a separate carrier wafer and afterwards be bonded to the channel layer 70. The carrier wafer can be released before or after bonding of the contact layer. The forming of AgCl on top of Ag can also be done after patterning of the channel layer. Furthermore, the contact layer can be made in glass by means of sand blasting, after which the glass sheet can be bonded to the channel layer.

Any other approach for the fabrication of a system as described can also be used.

The foregoing description details certain embodiments of the invention. It will be appreciated, however, that no matter how detailed the foregoing appears in text, the invention may be practiced in many ways. It should be noted that the use of particular terminology when describing certain features or aspects of the invention should not be taken to imply that the terminology is being re-defined herein to be restricted to including any specific characteristics of the features or aspects of the invention with which that terminology is associated.

While the above detailed description has shown, described, and pointed out novel features of the invention as applied to various embodiments, it will be understood that various omissions, substitutions, and changes in the form and details of the device or process illustrated may be made by those skilled in the technology without departing from the spirit of the invention.

What is claimed is:

1. A micromachined free-diffusion liquid-junction reference electrode comprising:
    an internal electrode reservoir configured to contain an electrolyte;
    an internal electrode in the internal electrode reservoir configured to contact with the electrolyte when present;
    a pinhole configured to provide a fluidic contact to a sample solution; and
    at least one high-aspect-ratio channel connecting the internal electrode reservoir and the pinhole, wherein the electrolyte is configured to freely diffuse from the internal electrode reservoir to the pinhole through the high-aspect-ratio channel, wherein the at least one high-aspect-ratio channel has one or more of an inlet part connected to the internal electrode reservoir, an outlet part connected to the pinhole, and a folded geometry in between the inlet part and the outlet part, wherein the reference electrode further comprises at least one electrically conductive strip configured to form a low impedance bypass for the high-aspect-ratio channel, wherein the electrically conductive strip is configured to connect the inlet part of the high-aspect-ratio channel closest to the electrolyte reservoir comprising the internal electrode and the outlet part of the high-aspect ratio channel.

2. The micromachined reference electrode according to claim 1, wherein the aspect ratio of the at least one high-aspect-ratio channel is from about 100:1 to 10000:1.

3. The micromachined reference electrode according to claim 1, wherein the aspect ratio of the at least one high-aspect-ratio channel is from about 250:1 to 5000:1.

4. The micromachined reference electrode according to claim 1, wherein the aspect ratio of the at least one high-aspect-ratio channel is from about 500:1 to 2500:1.

5. The micromachined reference electrode according to claim 1, wherein the electrically conductive strip is configured to connect the inlet part of the high-aspect-ratio channel closest to the electrolyte reservoir comprising the internal electrode and the outlet part of the high-aspect ratio channel closest to the pinhole.

6. The micromachined reference electrode according to claim 1, wherein the internal electrode is an Ag/AgCl electrode and/or wherein the electrolyte is a KCl solution.

7. The micromachined reference electrode according to claim 1, wherein the internal electrode is an IrOx electrode and/or wherein the electrolyte is a fixed pH solution.

8. The micromachined reference electrode according to claim 1, wherein the reference electrode comprises at least one additional electrolyte reservoir connected to at least one second high-aspect-ratio channel, where the at least one additional electrolyte reservoir and the at least one second high-aspect-ratio channel are connected to and provided in between the internal electrode reservoir and the pinhole.

9. The micromachined reference electrode according to claim 1, wherein the liquid-junction reference electrode further comprises at least one additional element selected from a group comprising an external electrical contact to the internal electrode, a device for filling the reservoir, and an additional electrode forming an ion conductivity sensor.

10. The micromachined reference electrode according to claim 1, wherein the channel is substantially free of hydrogel, polyelectrolyte, and porous ceramic.

11. The micromachined reference electrode according to claim 1, wherein the at least one high-aspect-ratio channel comprises an ionic liquid a solvent and/or ion conducting plug.

12. A sensor comprising at least one micromachined reference electrode according to claim 1, the sensor further comprising:
an external potentiostat,
an electronic circuit comprising at least one of the following: a read-out device, digital processor, RF-communicator, electronic compensator, analog processor, and electronic converter.

13. The sensor according to claim 12, wherein the sensor is an electrochemical sensor, an amperometric sensor, or a potentiometric sensor.

14. A device comprising a micromachined reference electrode according to claim 1.

15. A device according to claim 14, wherein the device is a microfluidic system or a microfluidic chip.

16. A device according to claim 14, the device further comprising one or more of a reactor chamber, a liquid inlet, a liquid outlet, an electrical connection, a pump, and a valve.

17. A system in package comprising a device according to claim 14, further comprising an external power supply.

18. The system in package according to claim 17, further comprising an integrated circuit bonded to a microfluidic system.

19. A micromachined free-diffusion liquid-junction reference electrode comprising:
means for containing an electrolyte;
means for contacting with the electrolyte when present;
means for providing a fluidic contact to a sample solution; and
means for connecting the containing means and the contact providing means,
wherein the electrolyte is configured to freely diffuse from the containing means to the contact providing means through the connecting means,
wherein the connecting means has one or more of an inlet part connected to the containing means, an outlet part connected to the contact providing means, and a folded geometry in between the inlet part and the outlet part,
wherein the reference electrode further comprises at least one electrically conductive strip configured to form a low impedance bypass for the connecting means, wherein the electrically conductive strip is configured to connect the inlet part of the connecting means closest to the containing means and the outlet part of the connecting means.

20. The micromachined reference electrode according to claim 7, wherein the fixed pH solution is phosphate buffered saline.

* * * * *